(12) United States Patent
Madjarov

(10) Patent No.: US 10,786,345 B2
(45) Date of Patent: Sep. 29, 2020

(54) INTRAVASCULAR DEVICE FOR HEMIARCH REPAIR AND ASSOCIATED METHOD

(71) Applicant: THE CHARLOTTE-MECKLENBURG HOSPITAL AUTHORITY, Charlotte, NC (US)

(72) Inventor: Jeko Metodiev Madjarov, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 379 days.

(21) Appl. No.: 15/325,900

(22) PCT Filed: Jul. 21, 2015

(86) PCT No.: PCT/US2015/041228
§ 371 (c)(1),
(2) Date: Jan. 12, 2017

(87) PCT Pub. No.: WO2016/014452
PCT Pub. Date: Jan. 28, 2016

(65) Prior Publication Data
US 2017/0143468 A1    May 25, 2017

Related U.S. Application Data

(60) Provisional application No. 62/026,875, filed on Jul. 21, 2014.

(51) Int. Cl.
*A61F 2/06* (2013.01)
*A61F 2/07* (2013.01)

(52) U.S. Cl.
CPC .............. *A61F 2/064* (2013.01); *A61F 2/07* (2013.01); *A61F 2002/061* (2013.01); *A61F 2230/0069* (2013.01); *A61F 2250/0063* (2013.01)

(58) Field of Classification Search
CPC ....... A62F 2/064; A62F 2/07; A61F 2002/061
See application file for complete search history.

(56) References Cited

U.S. PATENT DOCUMENTS

2006/0217796 A1    9/2006  DiMatteo et al.
2009/0088833 A1    4/2009  Soetermans
(Continued)

FOREIGN PATENT DOCUMENTS

| DE | 20100443 U1 | 6/2001 |
| WO | 9819629 A2 | 5/1998 |
| WO | 2006028925 A1 | 3/2006 |

OTHER PUBLICATIONS

European Patent Office. International Search Report dated Oct. 9, 2015. International Application No. PCT/US2015/041228. Name of Applicant: The Charlotte-Mecklenburg Hospital Authority D/B/A Carolinas HealthCare System. English Language. 4 pages.

*Primary Examiner* — Christopher D. Prone
*Assistant Examiner* — Christine L Nelson
(74) *Attorney, Agent, or Firm* — J. Clinton Wimbish; Nexsen Pruet, PLLC

(57) ABSTRACT

Vascular devices and methods for addressing pathologies in the hemiarch of the aorta are provided. The device includes a main body and a secondary body. The main body has ends that are designed to be connected to corresponding ends of the native blood vessel. The secondary body has a free end and a fixed end that is engaged with an inner surface of the main body. The vascular device is movable from a retracted configuration, in which the secondary body is at least partially contained within the main body and the free end is on a proximal side of the fixed end, to an extended configuration, in which the secondary body is extended distally from the main body and the free end is on a distal side of the fixed end to address defects in the aorta downstream of the hemiarch.

20 Claims, 12 Drawing Sheets

(56) References Cited

U.S. PATENT DOCUMENTS

2013/0282103 A1* 10/2013 Madjarov .................. A61F 2/06
                                                      623/1.15
2014/0316513 A1* 10/2014 Tang ..................... A61F 2/2412
                                                      623/1.16

* cited by examiner

INTRAVASCULAR DEVICE FOR HEMIARCH REPAIR AND ASSOCIATED METHOD

CROSS REFERENCE TO RELATED APPLICATIONS

This application is a U.S. national stage application under 35 U.S.C. § 371 of International Application No. PCT/US2015/041228, filed on Jul. 21, 2015, which claims priority pursuant to 35 U.S.C. § 119(e) to U.S. Provisional Patent Application Ser. No. 62/026,875, filed on Jul. 21, 2014, each of which is hereby incorporated by reference in its entirety.

FIELD

The present disclosure relates generally to methods and apparatuses for therapy of aortic pathology. More specifically, methods and apparatuses are described for treating vascular abnormalities in the aorta, including in cases where hemiarch resection is needed. Methods and apparatuses are also described for addressing target sites in other areas of the aorta following hemiarch replacement.

BACKGROUND

Vascular abnormalities can be serious medical conditions that require prompt and effective treatment. An aneurysm, for example, is a bulging or ballooning portion of the wall of a blood vessel, usually an artery, that is the result of a weakened area of the artery wall. As the aneurysm enlarges, the walls of the artery become thinner, and the risk of rupture increases. A ruptured aneurysm can cause severe hemorrhaging, other complications, and death. Weakened walls of the arteries can be hereditary or can be caused by disease, such as arteriosclerosis.

In some cases, a tear may develop in the inner layer of the aorta, and blood may flow through the tear into the middle layer of the aorta, as shown in FIG. 1. This blood flow may cause the inner and middle layers of the aorta to separate and create a false lumen. This is known as a dissection. Dissections can be fatal if the false lumen ruptures the outside aortic wall. Moreover, a dissection may cause malperfusion, which may limit or cut off blood flow through the aorta or its branches to one or more organs.

In such cases, prompt and effective medical attention is necessary to reduce the risk of patient mortality. Conventional methods of treating vascular conditions such as aortic dissections, however, carry with them additional risks to the health of the patient, especially in the elderly.

Accordingly, there is a need for a method and apparatus for treating aortic abnormalities in a way that minimizes the risks to the patient, is reproducible, and is simple to administer.

BRIEF SUMMARY

A device and method are provided in accordance with an example embodiment for treating aortic abnormalities, in particular abnormalities that require resection of a portion of the aorta, such as in the region of the hemiarch. In one embodiment, a vascular device that replaces at least part of a patient's hemiarch is described. The vascular device comprises a main body and a secondary body. The main body has a first end and a second end, and each of the first and second ends attaches to a corresponding end of a native blood vessel to provide a pathway for blood flow from the patient's heart to vasculature distal to the heart. The secondary body has a free end and a fixed end, and the fixed end is engaged with an inner surface of the main body to limit movement of the fixed end in an axial direction. The vascular device moves from a retracted configuration, in which the secondary body is at least partially or fully contained within the main body and the free end is on a proximal side of the fixed end, to an extended configuration, in which the secondary body is extended distally from the main body and the free end is on a distal side of the fixed end. In the extended configuration, the secondary body engages downstream portions of the patient's aorta with respect to a position of the main body.

In some cases, the secondary body may have or define an opening through an outer surface thereof. The opening may surround one or more aortic branches of the patient's aortic arch. The fixed end of the secondary body may be engaged with the inner surface of the main body so as to allow the secondary body to rotate about a longitudinal axis of the main body. The inner surface of the main body may comprise a track, and the fixed end of the secondary body may comprise a guide configured to ride within the track such that the secondary body is rotatable with respect to the main body. In some embodiments, the vascular device may further comprise a lock. The lock may be actuated by a user from outside the vascular device and may maintain the secondary body in a rotationally fixed position with respect to the main body.

In some embodiments, at least one of the first and second ends of the main body may comprise a flare, such that the respective flare is trimmable by a user to adjust a diameter of the respective first or second end to correspond to and accommodate a diameter of the corresponding end of the native blood vessel to be joined to the respective end of the main body. The vascular device may further comprise at least one sleeve configured to extend over a seam defined between a respective end of the main body and the corresponding end of the native blood vessel. The at least one sleeve may be attached to an outer surface of the main body. The at least one sleeve may move between a first position and a second position. In the first position, the at least one sleeve may have or be biased toward a rolled configuration, such that a respective one of the first or second end of the main body is exposed for connection to the corresponding end of the native blood vessel. In the second position, the sleeve may have or be biased toward an extended configuration, such that a surface of the sleeve is disposed opposite an outer surface of the main body proximate the respective one of the first or second ends and engages the seam. In some cases, the vascular device may comprise a first sleeve proximate the first end and a second sleeve proximate the second end.

In some embodiments, the secondary body may have a length that is longer than a length of the main body, such that, in the retracted configuration, the free end of the secondary body extends past a corresponding end of the main body.

In still other embodiments, a method is described for replacing at least part of a patient's hemiarch using a vascular device. The method may include disposing a vascular device in a patient's body for replacing a hemiarch portion of the patient's aorta, wherein the vascular device comprises a main body having a first end and a second end and a secondary body having a free end and a fixed end, wherein the fixed end of the secondary body is engaged with an inner surface of the main body to limit movement of the fixed end in an axial direction. The first end of the main body may be connected with a corresponding end of a native blood vessel. The vascular device may be moved from a retracted configuration, in which the secondary body is at least partially contained within the main body and the free end is on a proximal side of the fixed end, to an extended configuration, in which the secondary body is extended distally from the main body and the free end is on a distal side of the fixed end. The second end of the main body may be connected with a corresponding end of the native blood vessel.

In some embodiments, the secondary body may be rotated about a longitudinal axis of the main body to align an opening defined through an outer surface of the secondary body with one or more aortic branches of the patient's aortic arch. The secondary body may be rotated while the vascular device is in the retracted configuration. In some cases, a lock may be actuated from outside the vascular device to maintain the secondary body in a rotationally fixed position with respect to the main body once the secondary body is rotated to a desired alignment with respect to the aortic branches of the patient's aortic arch.

In some embodiments, at least one of the first and second ends of the main body may comprise a flare, and the method may further comprise trimming a portion of the respective flare to adjust a diameter of the respective first or second end to correspond to and accommodate a diameter of the corresponding end of the native blood vessel to be joined to the respective end of the main body. Furthermore, in some cases, a portion of the free end of the secondary body may be trimmed.

In some cases, a sleeve of the vascular device may be moved from a first position, in which the sleeve is biased toward a rolled configuration such that a respective one of the first or second ends of the main body is exposed for connection to the respective end of the native blood vessel, to a second position, in which the sleeve is biased toward an extended configuration such that a surface of the sleeve is disposed opposite an outer surface of the main body proximate the respective one of the first or second ends and engages a seam defined between a respective end of the main body and the corresponding end of the native blood vessel. Moving a sleeve of the vascular device may comprise moving a first sleeve disposed proximate the first end of the main body to engage a seam defined between the first end of the main body and the corresponding end of the native blood vessel. The second end of the main body may be connected with a corresponding end of the native blood vessel, such that a pathway is provided for blood flow from the patient's heart to vasculature distal to the heart via the main body and the secondary body.

BRIEF DESCRIPTION OF THE DRAWINGS

Figure 1:
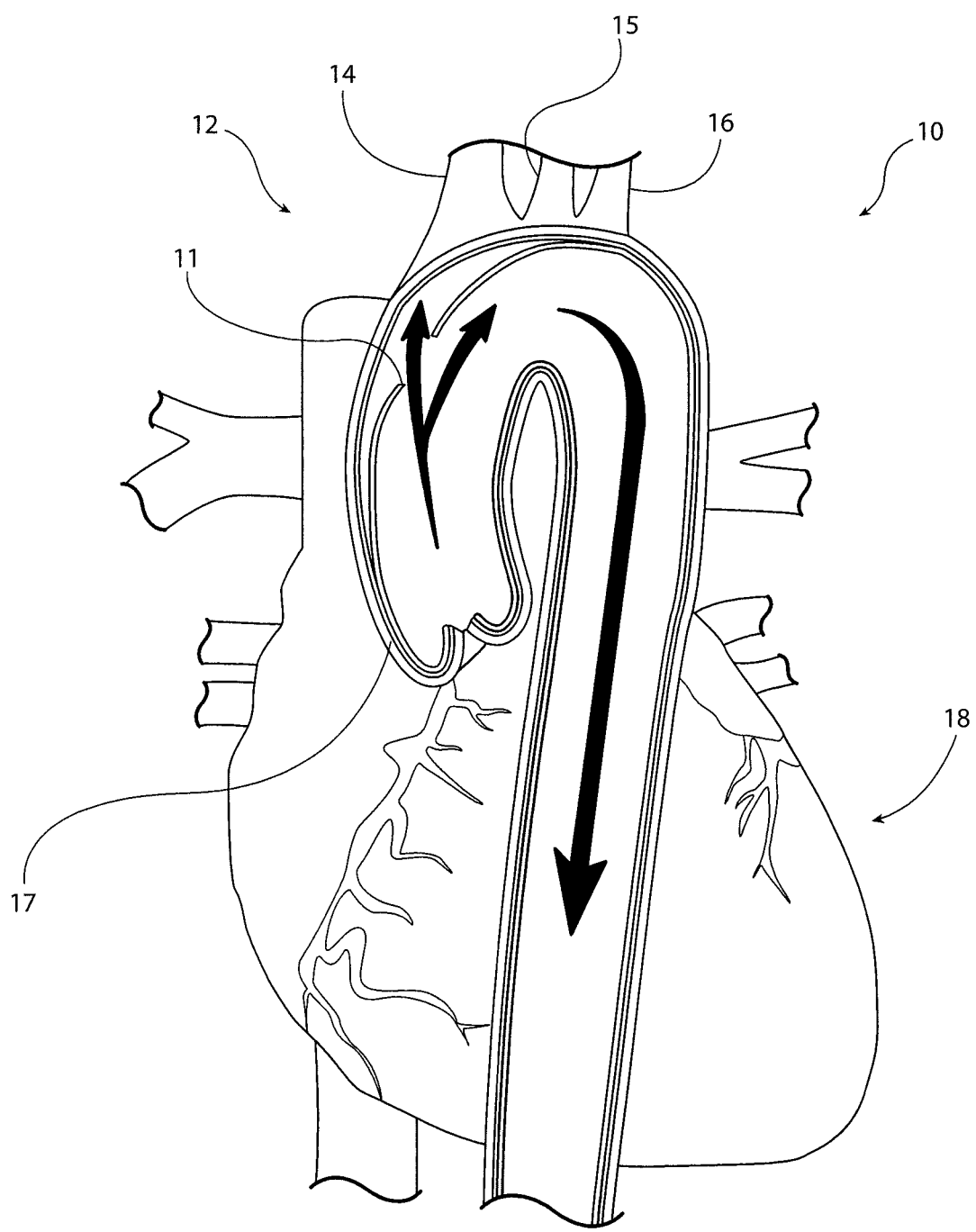
Figure 2A:
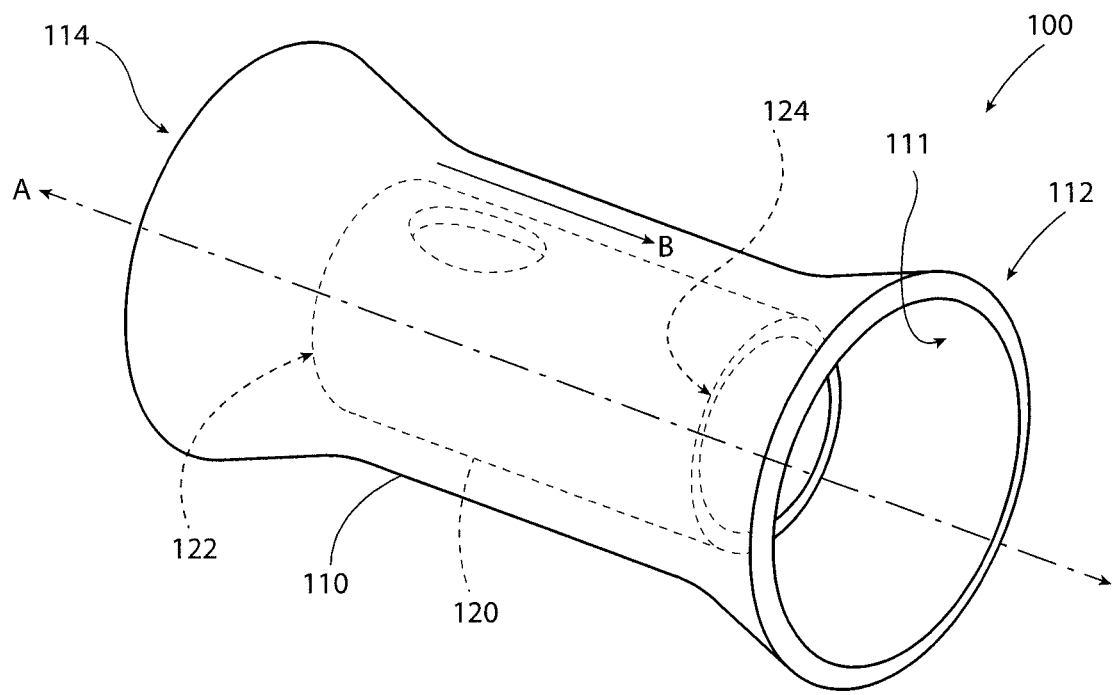
Figure 2B:
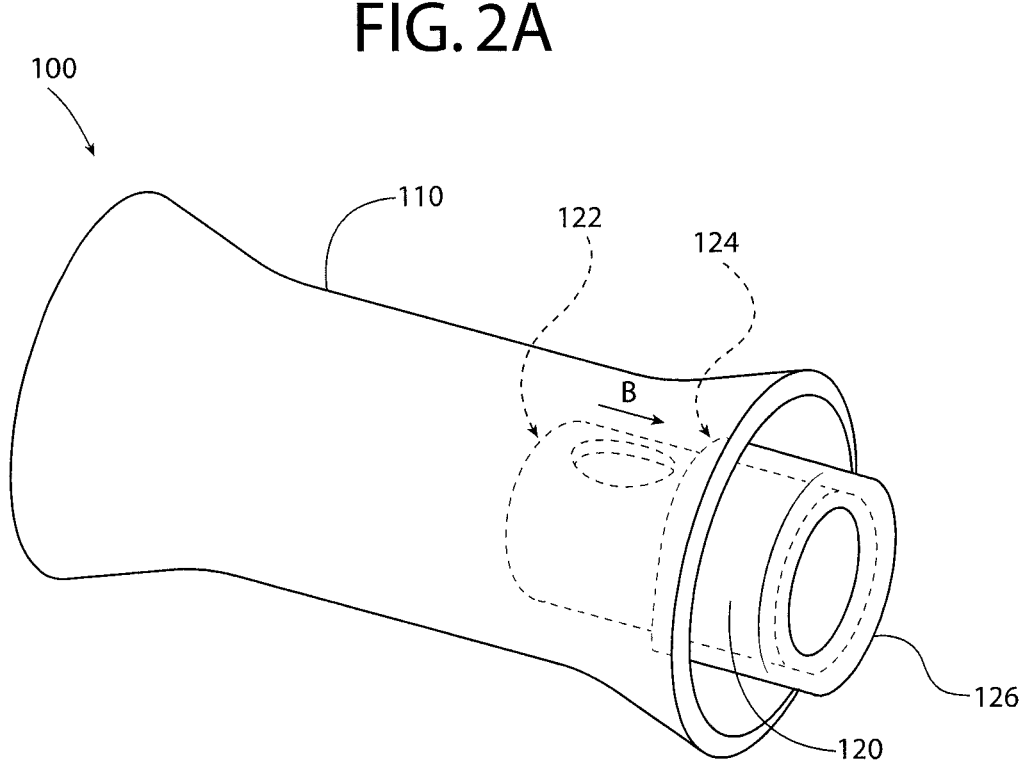
Figure 2C:
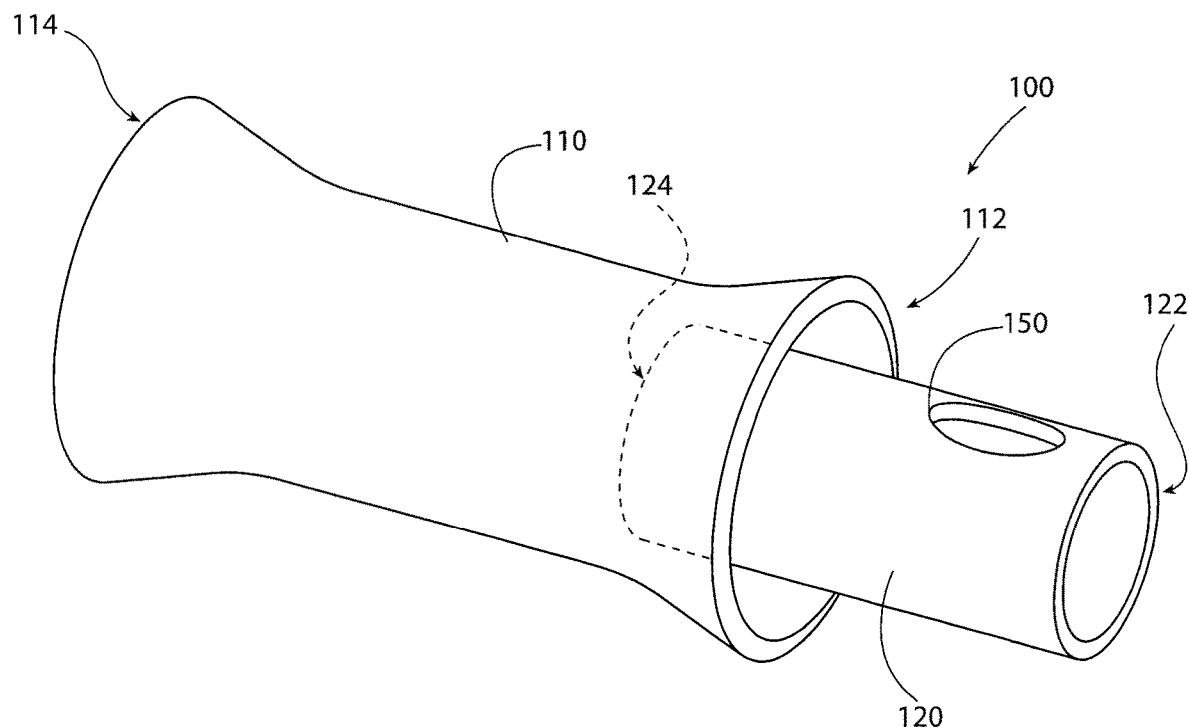
Figure 3A:
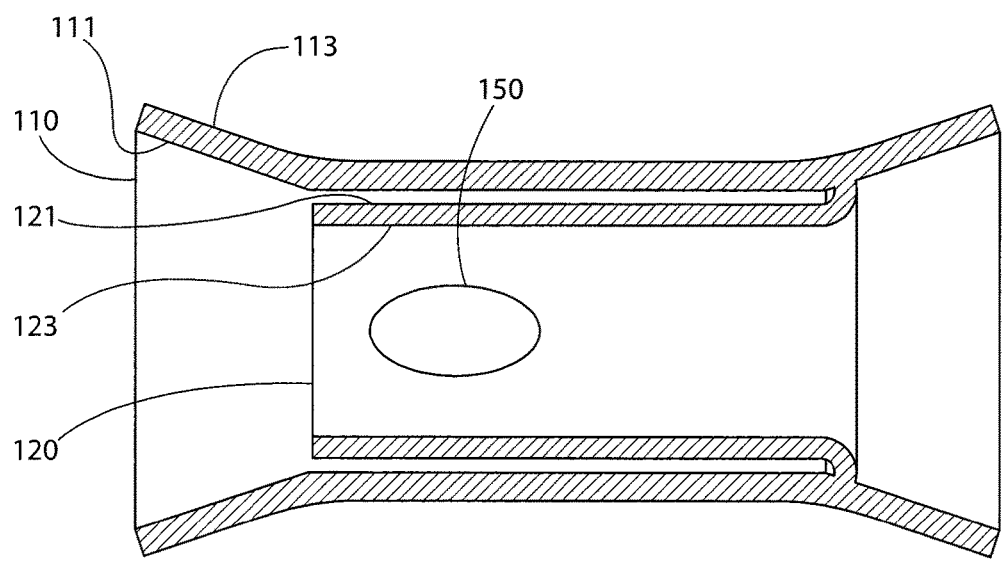
Figure 3B:
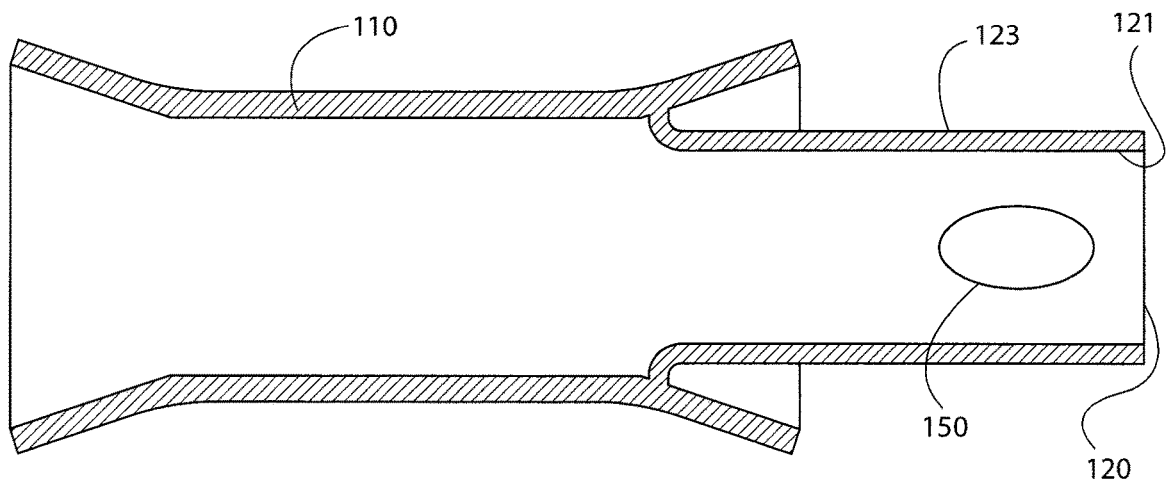
Figure 4A:
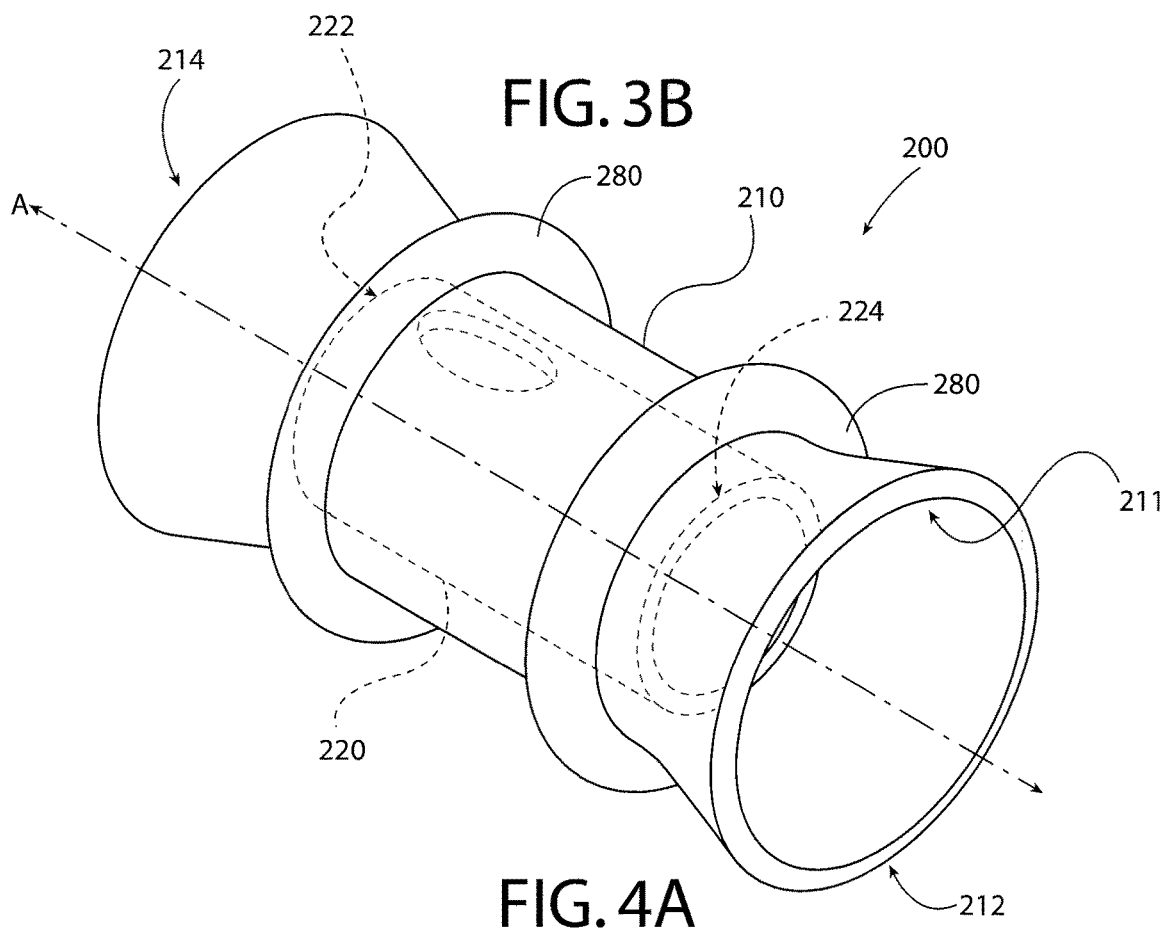
Figure 4B:
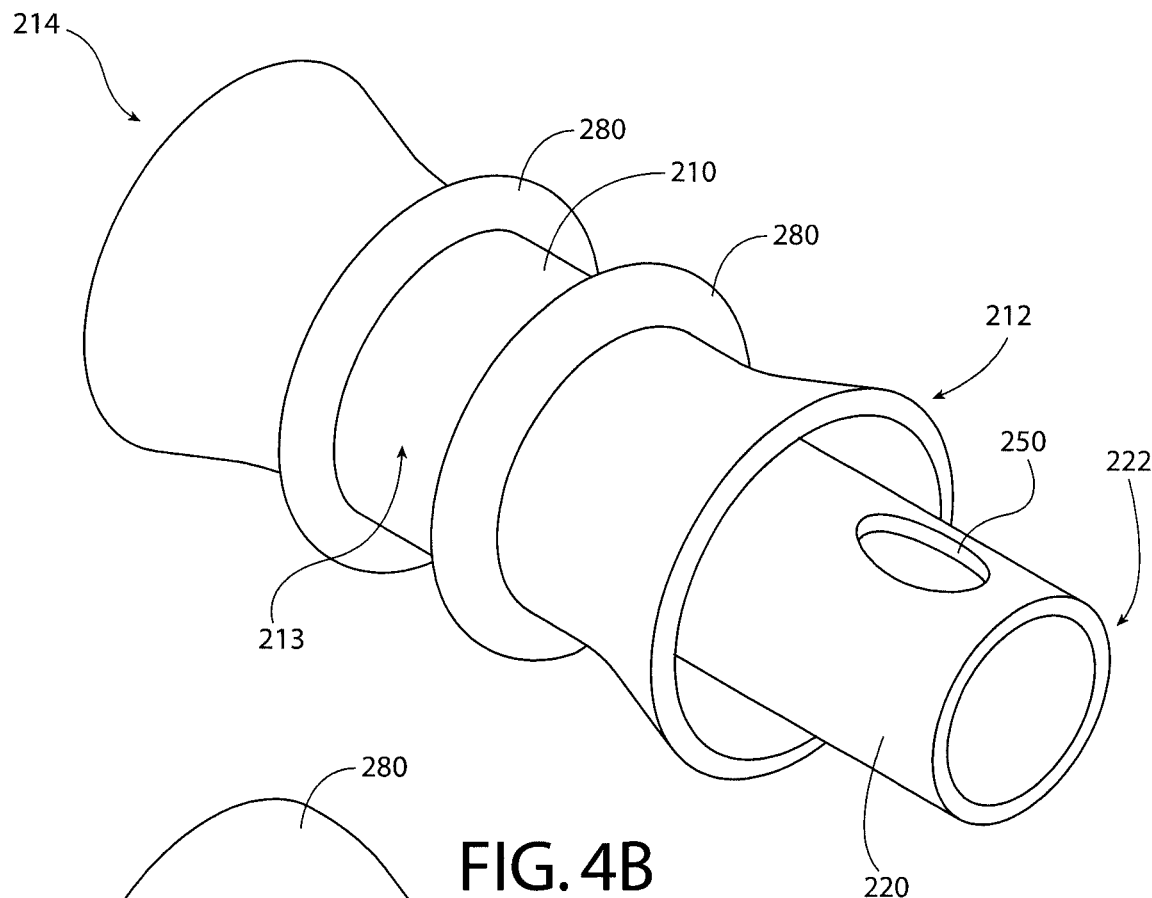
Figure 4C:
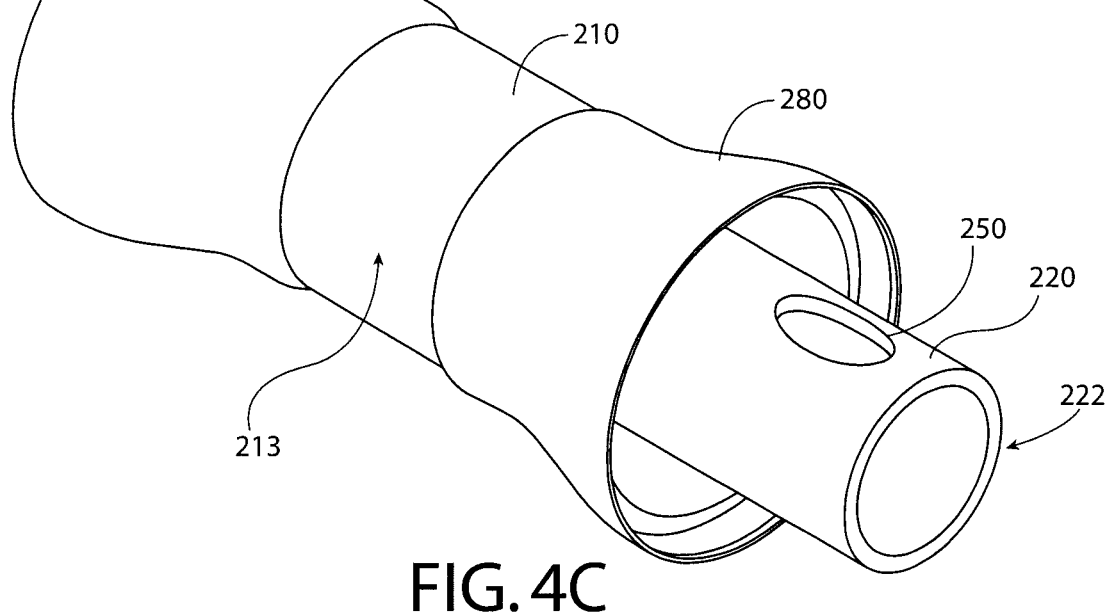
Figure 5A:
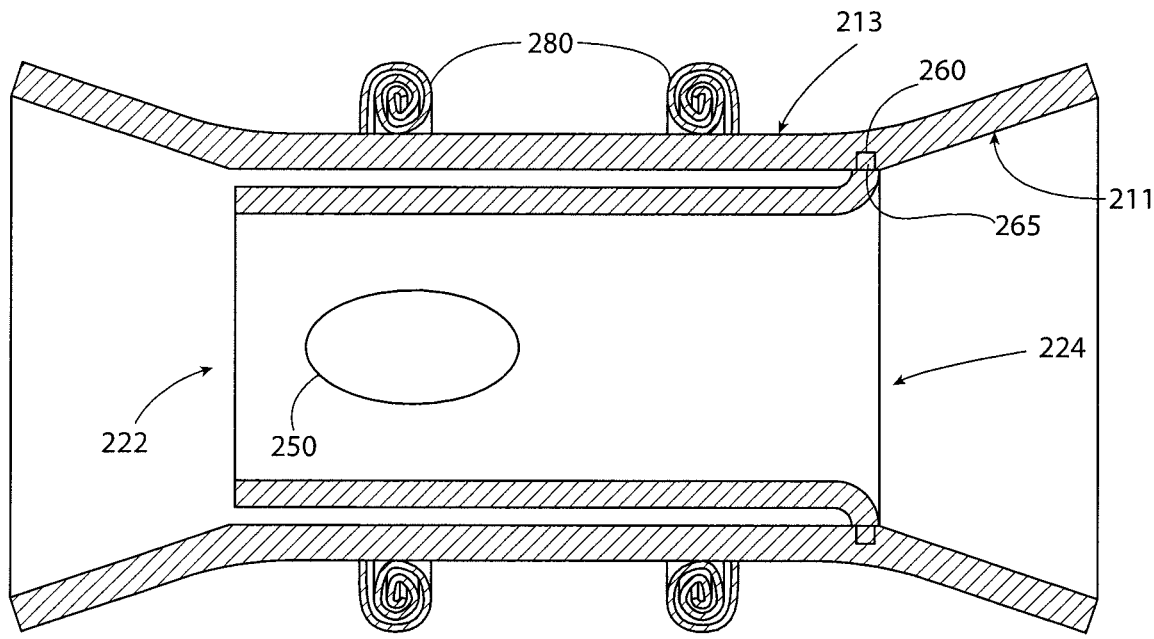
Figure 5B:
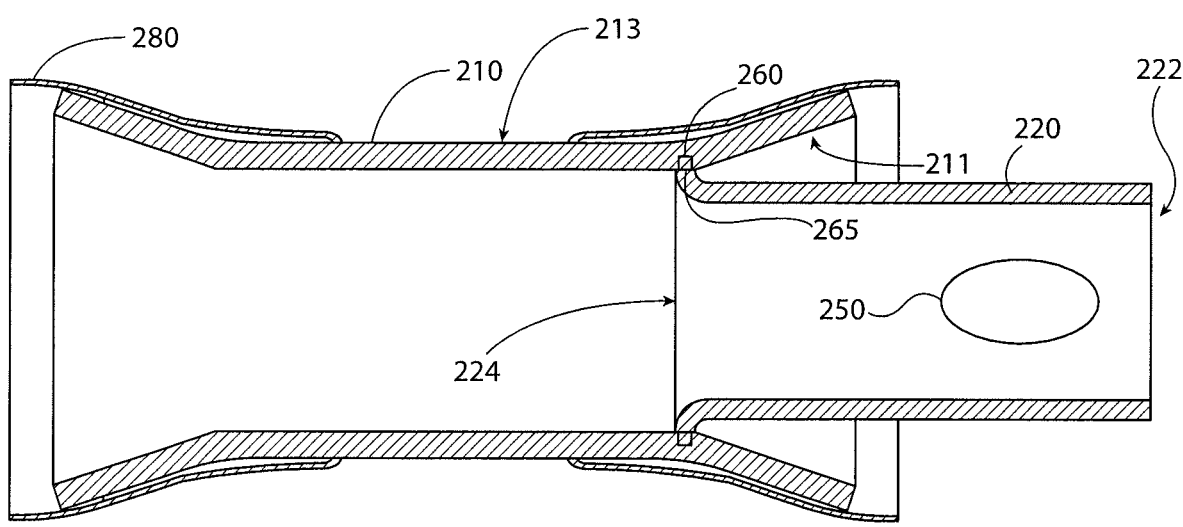
Figure 6A:
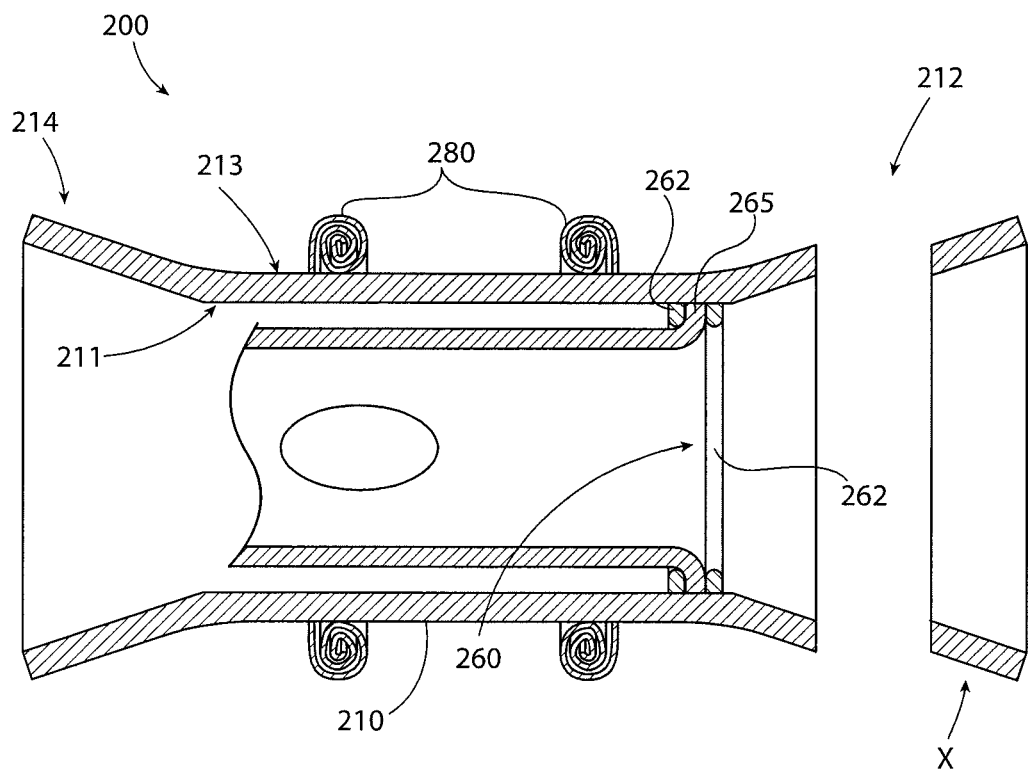
Figure 6B:
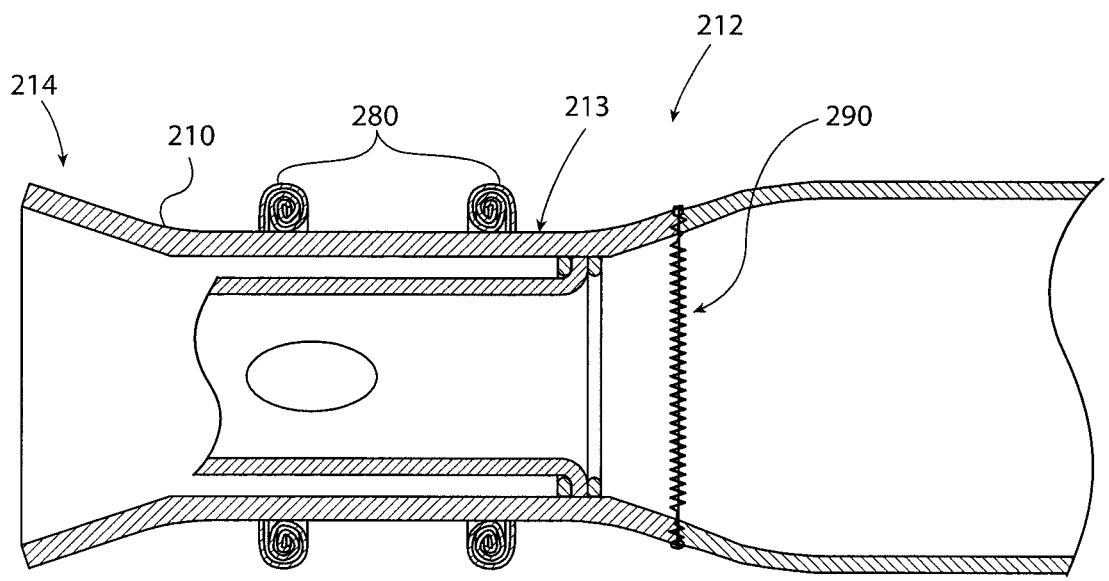
Figure 6C:
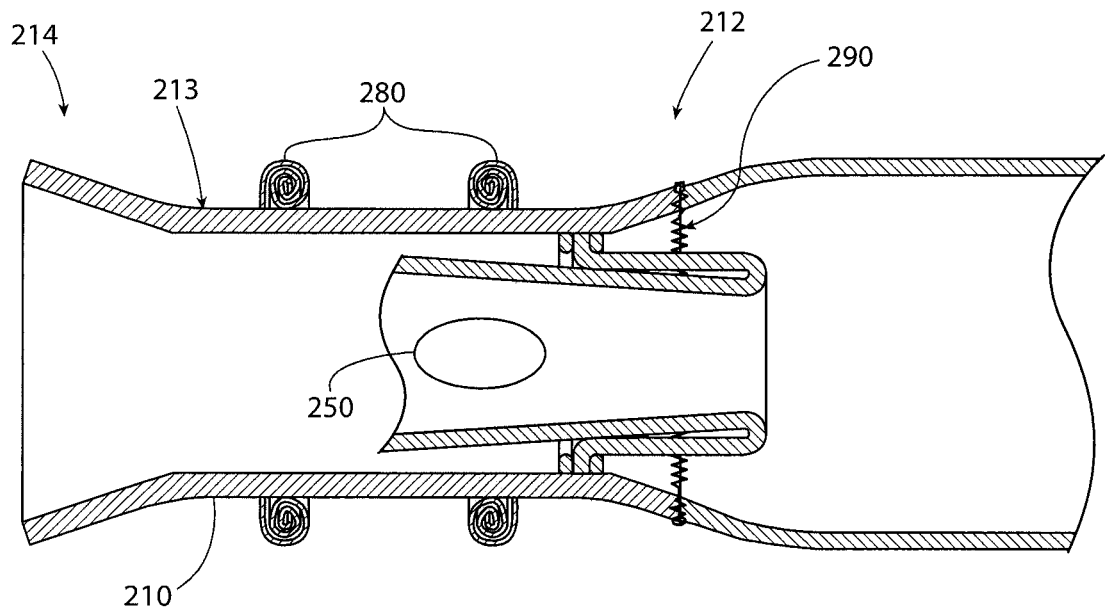
Figure 6D:
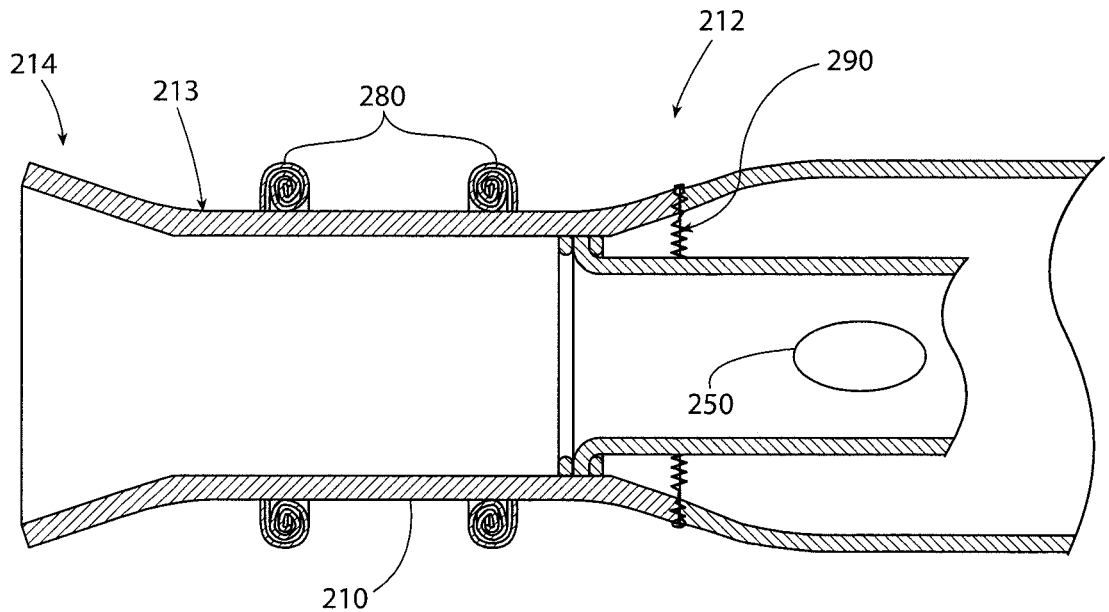
Figure 6E:
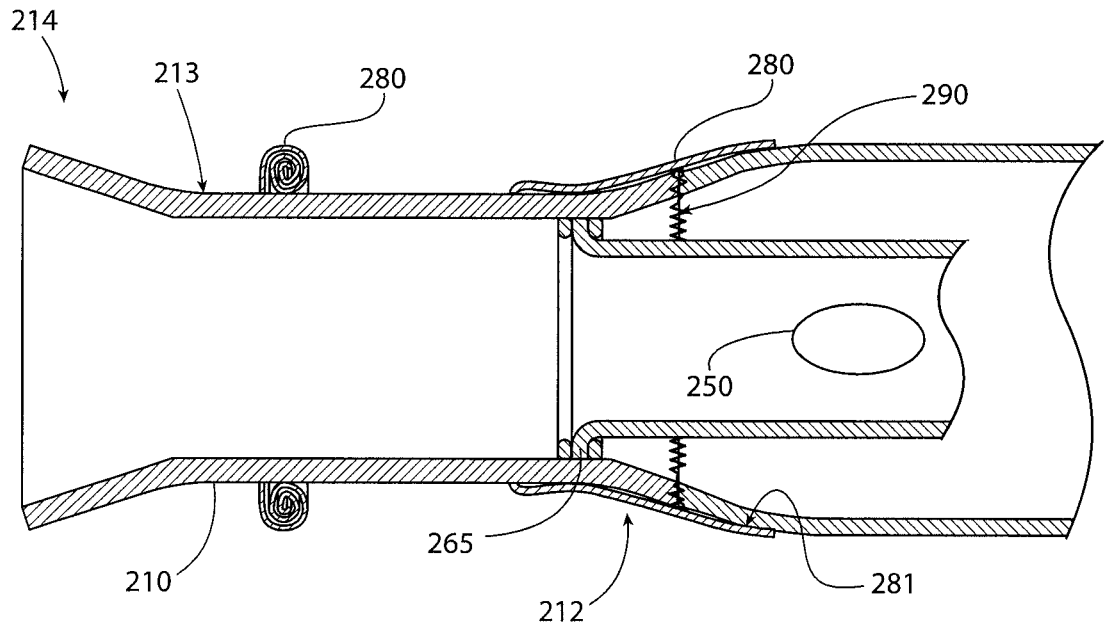
Figure 7A:
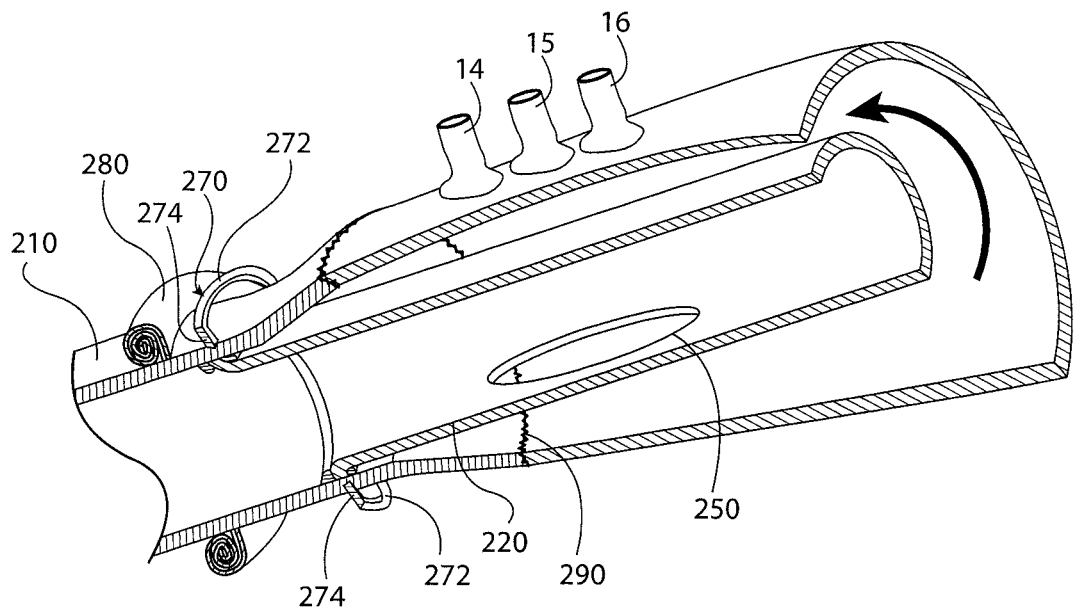
Figure 7B:
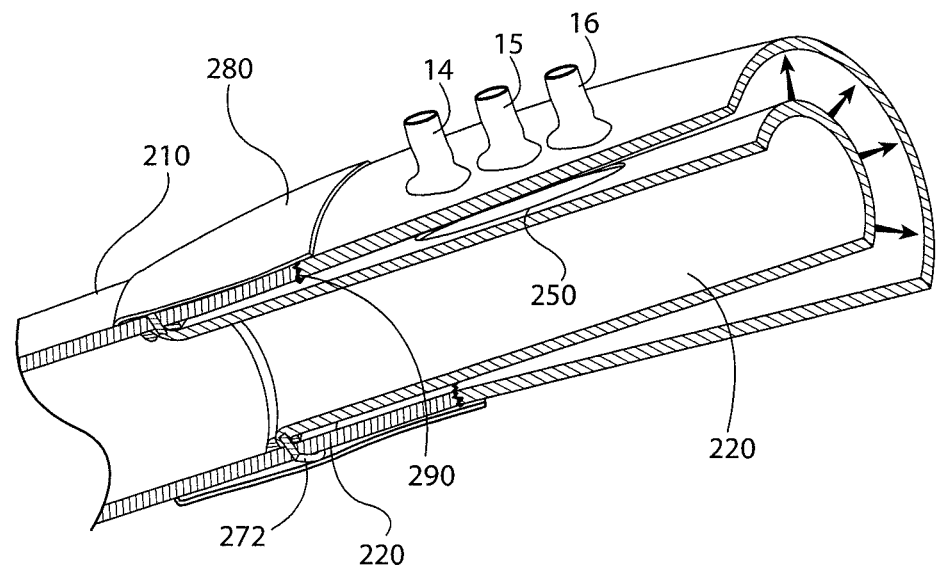
Figure 8A:
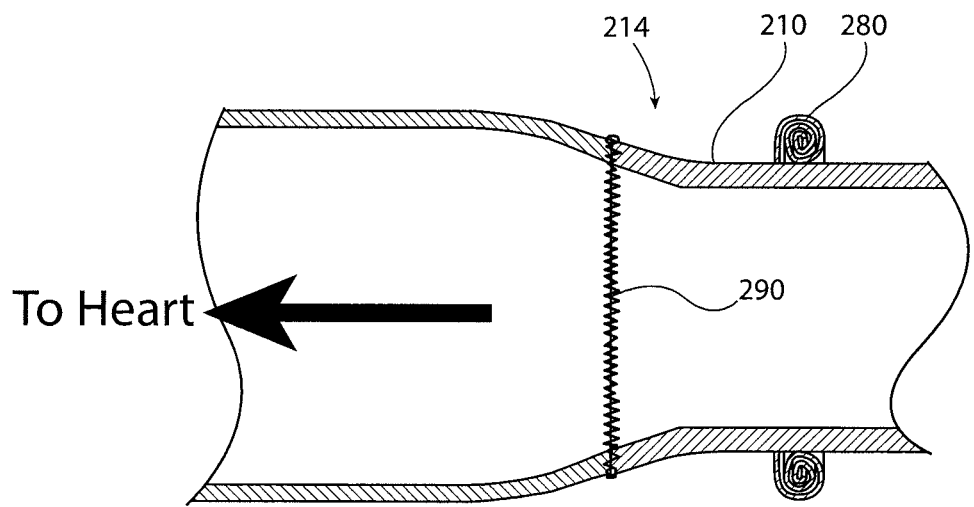

Having thus described the invention in general terms, reference will now be made to the accompanying drawings, which are not necessarily drawn to scale, and wherein:

FIG. 1 shows a schematic representation of a dissection in the aortic arch;

FIG. 2A shows a schematic perspective representation of a vascular device in a retracted configuration in accordance with an exemplary embodiment of the present disclosure;

FIG. 2B shows a schematic perspective representation of the vascular device of FIG. 2A in an intermediate configuration between the retracted configuration of FIG. 2A and an extended configuration shown in FIG. 2C in accordance with an exemplary embodiment of the present disclosure;

FIG. 2C shows a schematic perspective representation of the vascular device of FIG. 2A and FIG. 2B in the extended configuration in accordance with an exemplary embodiment of the present disclosure;

FIG. 3A shows a cross-sectional representation of the vascular device of FIG. 2A in accordance with an exemplary embodiment of the present disclosure;

FIG. 3B shows a cross-sectional representation of the vascular device of FIG. 3A in the extended configuration in accordance with an exemplary embodiment of the present disclosure;

FIG. 4A shows a schematic perspective representation of a vascular device in a retracted configuration with sleeves in a first position in accordance with another exemplary embodiment of the present disclosure;

FIG. 4B shows a schematic perspective representation of a vascular device in an extended configuration with sleeves in a first position in accordance with another exemplary embodiment of the present disclosure;

FIG. 4C shows a schematic perspective representation of a vascular device in an extended configuration with sleeves in a second position in accordance with another exemplary embodiment of the present disclosure;

FIG. 5A shows a cross-sectional representation of a vascular device in the retracted configuration in accordance with another exemplary embodiment of the present disclosure;

FIG. 5B shows a cross-sectional representation of the vascular device of FIG. 5A in the extended configuration in accordance with an exemplary embodiment of the present disclosure;

FIG. 6A shows a cross-sectional representation of a vascular device in the retracted configuration with a section of the first end trimmed in accordance with an exemplary embodiment of the present disclosure;

FIG. 6B shows a cross-sectional representation of the vascular device of FIG. 6A in the retracted configuration sutured to a corresponding end of the native vessel in accordance with an exemplary embodiment of the present disclosure;

FIG. 6C shows a cross-sectional representation of the vascular device of FIG. 6B in an intermediate configuration between the retracted configuration and the extended configuration in accordance with an exemplary embodiment of the present disclosure;

FIG. 6D shows a cross-sectional representation of the vascular device of FIG. 6C in the extended configuration in accordance with an exemplary embodiment of the present disclosure;

FIG. 6E shows a cross-sectional representation of the vascular device of FIG. 6D in the extended configuration with the first sleeve moved to the second position in accordance with an exemplary embodiment of the present disclosure;

FIG. 7A shows a schematic perspective representation of the vascular device of FIGS. 6A-6E illustrating rotation and locking of the secondary body in accordance with an exemplary embodiment of the present disclosure;

FIG. 7B shows a schematic perspective representation of the vascular device of FIG. 7A showing the opening of the secondary body aligned with the aortic branches in accordance with an exemplary embodiment of the present disclosure;

FIG. 8A shows a cross-sectional representation of the second end of the main body of the vascular device of FIGS.

Figure 8B:
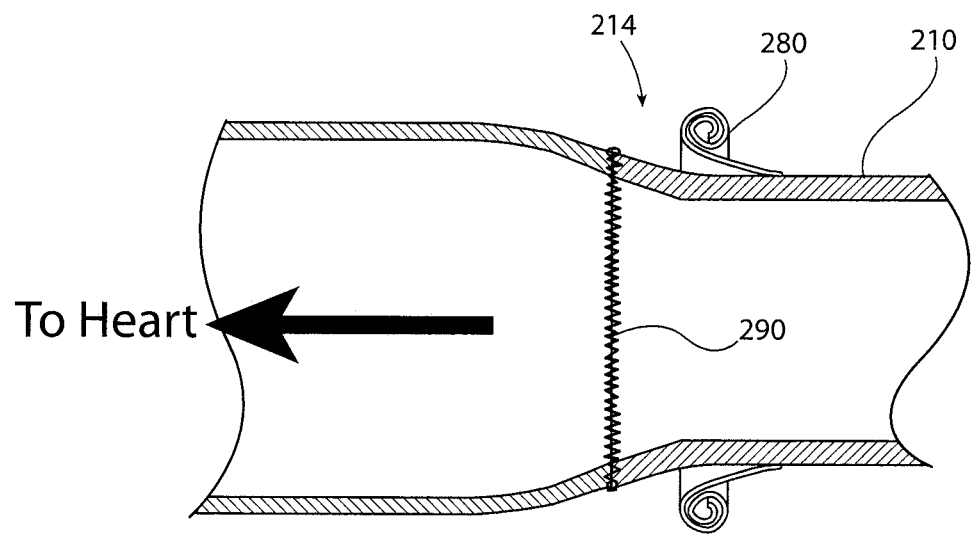
Figure 8C:
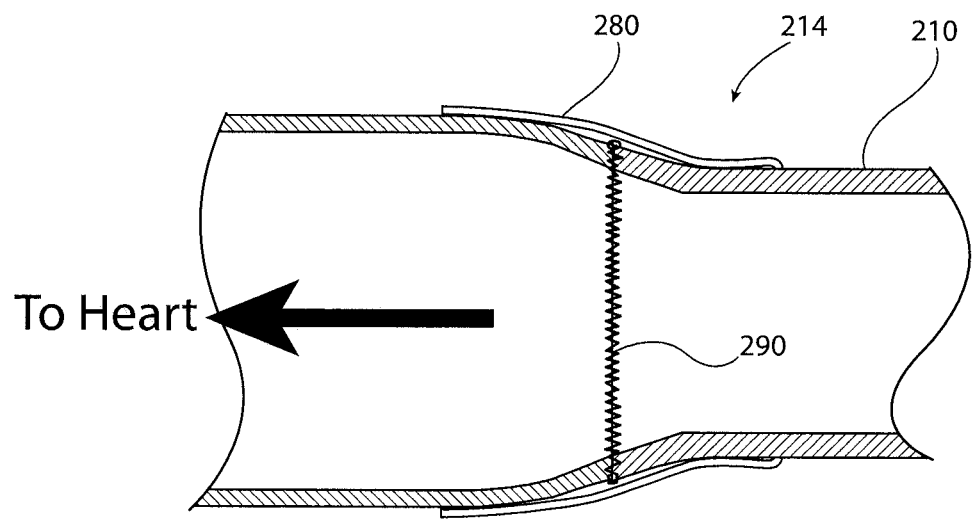
Figure 9:
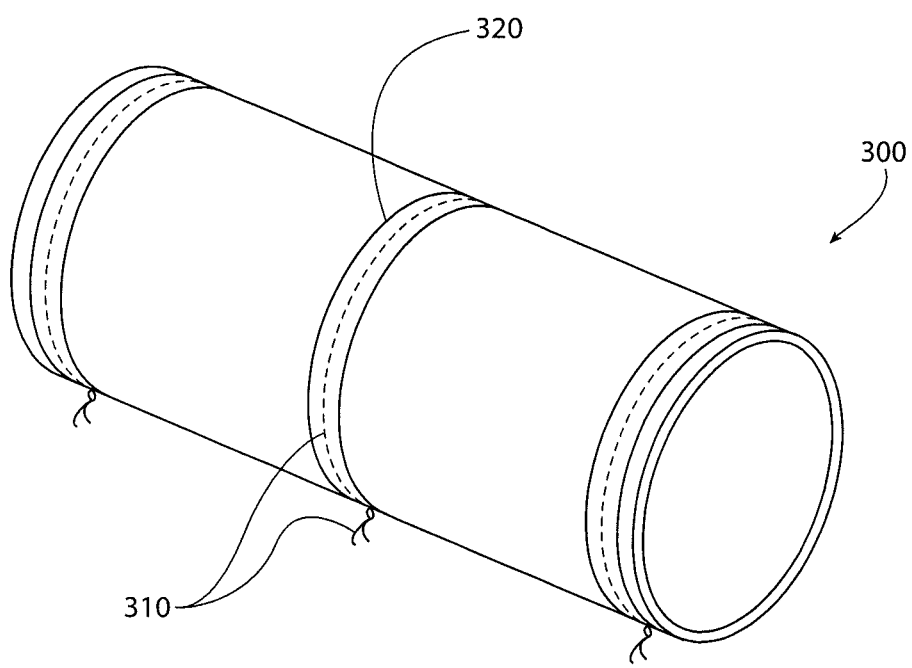

6A-6E connected to the corresponding end of the native vessel in accordance with an exemplary embodiment of the present disclosure;

FIG. 8B shows a cross-sectional representation of the second end of the main body of the vascular device of FIG. 8A with the second sleeve in an intermediate position between the first position of FIG. 8A and the second position of FIG. 8C in accordance with an exemplary embodiment of the present disclosure;

FIG. 8C shows a cross-sectional representation of the second end of the main body of the vascular device of FIG. 8A with the second sleeve in the second position in accordance with an exemplary embodiment of the present disclosure; and FIG. 9 shows a sleeve that is separate from the vascular device in accordance with an exemplary embodiment of the present disclosure.

DETAILED DESCRIPTION

Some embodiments of the present disclosure will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" to the heart refer to a location farthest from the heart; the terms "proximal" and "proximally" refer to a location closest to the heart. Furthermore, although the examples described herein refer to a dissection in the aortic arch, embodiments of the devices and methods described herein may be used to treat various vascular abnormalities requiring resection of a portion of the aorta, including aneurysms, type A dissections, and type B dissections, and in particular may be used to treat abnormalities that require resection of the hemiarch or a portion thereof.

Thoracoabdominal aortic pathologies are often considered some of the most difficult aortic pathologies to treat. A schematic illustration of the aorta 10 is shown in FIG. 1. The ascending aorta and the aortic arch 12, for example, are sections that include a high degree of curvature, as well as arteries that branch up to feed oxygenated blood to the head, neck, and arms. Such arteries include the innominate artery 14, the left common carotid artery 15, and the left subclavian artery 16.

Aortic abnormalities, such as dissections 11, are some of the most serious conditions that can affect the aorta and often must be addressed immediately and effectively to minimize the patient's risk of death. In fact, it may be said that 50% of patients suffering from acute type A aortic dissections (i.e., dissections 11 involving the aortic arch 12, an example of which is shown in FIG. 1) are dead within 48 hours of the occurrence of the dissection.

Conditions such as dissections often require that the damaged section of the aorta be cut out and removed and that a prosthetic graft be sutured to the sections of native aorta that remain to take the place of the resected section. For example, in a case such as the one pictured in FIG. 1, a section of the aorta extending from just above the aortic root 17 (proximate the junction of the aorta with the heart 18) to the aortic arch, proximate the innominate artery 14, known as the hemiarch, may need to be removed to address the dissection 11. Preoperative procedures including intravascular ultrasound (IVUS) measurements and/or computerized tomography (CT) or computerized axial tomography (CAT) scans may be used to allow the surgeon to select an appropriate prosthetic graft (e.g., one having the correct size and shape). It is often difficult in a preoperative setting, however, to obtain an accurate assessment of the condition of the vessel portion to be resected, the extent (e.g., length) of the resection, the diameter of the remaining portions of the native vessels, etc., such that a conventional prosthetic graft selected based on preoperative measurements may not be sized appropriately to address the actual condition as observed during the operative procedure.

Moreover, in conventional hemiarch procedures, multiple intravascular devices may need to be used in combination to repair the damaged portion of the patient's aorta. For example, a graft may be needed to replace the patient's hemiarch, and another device (e.g., an endograft) may be attached to a distal end of the graft to address conditions in the aortic arch and/or descending aorta. In some cases, the patient may require multiple surgeries, as issues may arise in other portions of the aorta following hemiarch replacement that were not present during the initial surgery to repair the hemiarch. Such post-operative surgeries may present new risks to the patient and increase the likelihood of medical complications, including risks of endoleaks and tearing of the native vessels.

Accordingly, embodiments of the present disclosure provide for a vascular device and method for addressing aortic pathologies that are configured to address a dissection originating in the hemiarch, and are at the same time flexible enough for addressing conditions in the aortic arch and other regions distal of the aortic arch, as necessary. In addition, embodiments of the present disclosure may be configured to allow a user (e.g., a surgeon) to adjust the size of a vascular device described herein (e.g., diameter and length) to adequately correspond to the actual size of the patient's vasculature in real time and as observed during the operative procedure. In still other aspects, embodiments of the present disclosure are configured to facilitate hemostasis at the junctions of the ends of a vascular device described herein with the native aorta to minimize or eliminate the risk of endoleaks.

With reference now to FIGS. 2A-2C, embodiments of a vascular device 100 configured for replacing at least part of a patient's hemiarch are shown. The vascular device 100 comprises a main body 110 and a secondary body 120. The main body 110 may have a first end 112 and a second end 114, where each of the first and second ends is configured to be attached to a corresponding end of a native blood vessel to provide a pathway for blood flow from the patient's heart to vasculature distal to the heart. The secondary body 120 may have a free end 122 and a fixed end 124. The fixed end 124 may be engaged with an inner surface 111 of the main body 110 to limit movement of the fixed end in an axial direction (e.g., in a direction along the central axis A of the main body 110). The fixed end 124 may be engaged with an inner surface 111 of the main body 110 in any manner not inconsistent with the objectives of the present disclosure, including with an adhesive or fastener. The fixed end 124 may also have or define a unitary structure with the inner surface 111 of the main body 110.

As such, some embodiments of the vascular device 100 may be configured to be moved from a retracted configuration, in which the secondary body 120 is at least partially contained within the main body 110 and the free end 122 of the secondary body 120 is on a proximal side of the fixed end 124, as shown in FIG. 2A, to an extended configuration, in which the secondary body 120 is extended distally from the main body (e.g., in a direction away from the heart) and the free end 122 is on a distal side of the fixed end 124. The vascular device 100 is shown in the extended configuration in FIG. 2C, with FIG. 2B showing an intermediate position of the vascular device 100, in which the secondary body 120 is partially everted.

For example, in the embodiment depicted in FIGS. 2A-2C and 3A-3B, the secondary body 120 is configured such that the free end 122 may be pushed (e.g., by a user) in a direction B, toward the fixed end 124, creating a folded edge 126 (shown in FIG. 2B) about which the secondary body 120 is turned outside-in. In other words, a surface 121 of the secondary body 120 that is the outer surface when the secondary body 120 is being held within the main body 110 and the vascular device 100 is in the retracted configuration, as shown in FIGS. 2A and 3A, may become an inner surface of the secondary body 120 once the vascular device 100 is in the extended (e.g., everted) configuration shown in FIGS. 2C and 3B. Likewise, the surface 123 of the secondary body 120 that is the inner surface when the vascular device 100 is in the retracted configuration of FIGS. 2A and 3A may become the outer surface of the secondary body 120 when the vascular device 100 has been moved to the extended configuration of FIGS. 2C and 3B.

Thus, in the retracted configuration of FIGS. 2A and 3A, the inner surface 111 of the main body 110 (as contrasted with an outer surface 113 of the main body 110) may be disposed proximate the surface 121 of the secondary body 120 that forms the outer surface in that position. Moreover, although FIG. 3A depicts a space between the inner surface 111 of the main body 110 and the surface 121 of the secondary body 120, in some cases the surfaces 111, 121 or at least a portion of those surfaces may be contacting each other, such as when the secondary body 120 is made of self-expandable material (e.g., Nitinol) and expands radially within the main body 110.

Embodiments of the vascular device 100 may be configured such that the first and second ends 112, 114 of the main body 110 can be connected to (e.g., sutured to) ends of the corresponding native vessel formed by resection of the patient's hemiarch. In this way, eversion of the secondary body 120 to move the secondary body 120 to the extended configuration shown in FIGS. 2C and 3B may serve to position the secondary body 120, or at least a portion of the secondary body, proximate the branch arteries 14, 15, 16 of the aortic arch 12 (shown in FIG. 1). Accordingly, to allow proper blood flow through the branch arteries 14, 15, 16, the secondary body 120 may, in some cases, define an opening 150 through the outer surface of the secondary body that is configured to surround one or more aortic branches 14, 15, 16 of the patient's aortic arch 12. In this way, the opening 150 according to some embodiments may be positioned at the junction of the aortic branches 14, 15, 16 with the aortic arch 12 and may provide a pathway for the blood to flow from the heart, through the main body 110 of the vascular device 100, into the secondary body 120 (when the vascular device is in the extended configuration), through the opening 150, and into each branch 14, 15, 16.

In some embodiments, the opening 150 may be configured to define a seal with the inner surface of the patient's blood vessel in the area of the aortic branches 14, 15, 16, so as to minimize or stop the leakage of blood into the space between the outer surface of the secondary body 120 and the inner surface of the blood vessel. For example, the opening 150 may define, in some cases, a rim, a bumper, or some other radially protruding feature (not shown) that is configured to contact the inner surface of the patient's blood vessel in the area of the aortic branches 14, 15, 16 and minimize the passage of blood into the space surrounding the outer surface of the secondary body 120. In still other cases, however, the area of the secondary body 120 surrounding and defining the opening 150 may be made of a mesh material (e.g., similar to a stent) so as to facilitate clotting, such that the blood clots formed may serve to promote a natural seal between the secondary body and the inner surface of the blood vessel.

To facilitate proper alignment of the opening 150 of the secondary body 120 with the aortic branches 14, 15, 16 shown in FIG. 1, in some embodiments the fixed end 124 of the secondary body 120 may be engaged with the inner surface 11 of the main body 110 in such a manner so as to allow the secondary body 120 to rotate about a longitudinal axis of the main body (e.g., central axis A of FIG. 2A). FIGS. 4A-7B, for example, depict another embodiment of a vascular device 200 that includes a main body 210 and a secondary body 220, similar to the main body 110 and secondary body 120 described above with reference to FIGS. 2A-3B.

In this regard, with reference to FIGS. 4A-5B, the main body 210 may have a first end 212 and a second end 214, where each of the first and second ends is configured to be attached to a corresponding end of a native blood vessel to provide a pathway for blood flow from the patient's heart to vasculature distal to the heart. The secondary body 220 may have a free end 222 and a fixed end 224. The fixed end 224 may be engaged with an inner surface 211 of the main body 210 (shown in FIGS. 4A and 5A) to limit movement of the fixed end in an axial direction (e.g., in a direction along the central axis A of the main body 210, shown in FIG. 4A).

As described above with respect to the vascular device 100, embodiments of the vascular device 200 may also be configured to be moved from a retracted configuration, in which the secondary body 220 is at least partially contained within the main body 210 and the free end 222 of the secondary body 220 is on a proximal side of the fixed end 224, as shown in FIGS. 4A and 5A, to an extended configuration, in which the secondary body 220 is extended distally from the main body (e.g., in a direction away from the heart) and the free end 222 is on a distal side of the fixed end 224, as shown in FIGS. 4B and 5B.

In some embodiments, the fixed end 224 of the secondary body 220 may be engaged with the inner surface 211 of the main body 210 so as to allow the secondary body 220 to rotate about a longitudinal axis of the main body 210 (e.g., the central axis A). For example, the inner surface 211 of the main body 210 may comprise a track 260, and the fixed end 224 of the secondary body 220 may include a guide 265 configured to be received by and ride within the track, such that the secondary body is rotatable with respect to the main body.

In FIGS. 5A and 5B, for example, the track 260 is depicted as being a groove circumferentially defined in the inner surface 211, and the guide 265 is an extension of the fixed end 224 of the secondary body 220 that is configured to fit within and be movable with respect to the groove of the track 260. In other embodiments, such as the embodiment depicted in FIGS. 6A-7B, the track 260 is defined by two parallel protruding ridges 262 that are formed by or attached to the inner surface 211 of the main body 210 and that extend along the circumference of the main body. In this case, the guide 265 may be a lip or ledge defined by or extending from the fixed end 224 of the secondary body 220 that is configured to fit within the space between the two ridges 262 and be movable with respect to the inner surface 211 of the main body 210. In still other embodiments, other types of engagements and mechanisms may be used to allow the secondary body 220 to rotate with respect to the main body 210, while maintaining the position of the fixed end 224 of the secondary body fixed with respect to the longitudinal axis of the main body, as described above.

In some cases, a locking mechanism may be provided to allow the rotational position of the secondary body 220 to be fixed, along with the axial position, with respect to the main body 210. The locking mechanism may be configured to be actuatable by a user from outside the vascular device 200 and may be configured to maintain the secondary body 220 in a rotationally fixed position with respect to the main body 210. In this way, once the secondary body 220 has been rotated to achieve proper alignment of the opening 250 with the arterial branches 14, 15, 16, the position of the secondary body can be locked in place.

With reference to FIG. 7A, for example, one embodiment of a lock 270 is shown that includes an actuating portion 272 and a locking extension 274. The actuating portion 272 may extend between two locking extensions 274 in some cases, and a user (e.g., the surgeon) may be able to move the locking extensions 274 into and out of engagement with the guide 265 (shown, e.g., in FIG. 6E) to fix the rotational position of the secondary body 220 with respect to the main body 210. In this regard, the locking extensions 274 may initially be engaged with the main body 210 (e.g., via holes formed in the main body), but may be spaced from and disengaged with respect to the guide 265 of the fixed end 224 of the secondary body 220, as shown in FIG. 7A. When a user has achieved the appropriate rotational position of the secondary body 220 (depicted by an arrow in FIG. 7A), the user may push on the actuating portion 272 of the lock 270 to move the locking extensions 274 into engagement with the guide 265 to lock it in place. In some embodiments, multiple locks 270 may be provided, distributed along an outer circumference of the vascular device 200, such that a user may need to actuate 2, 3, 4, or more locks 270 to effect rotational fixation of the position of the secondary body 220 with respect to the main body 210.

Turning again to FIGS. 4A-7B, in some embodiments the vascular device 200 may comprise at least one sleeve 280 that is configured to extend over a seam 290 (shown, e.g., in FIG. 6B) defined between a respective end of the main body 210 and the corresponding end of the native blood vessel. The sleeves 280 may be attached to an outer surface 213 of the main body 210, for example, such that they form part of the main body. In other cases, however, separate sleeves 300 may be provided, as shown in FIG. 9 and described in greater detail below.

The sleeves 280 shown in FIGS. 4A-7B may be configured to be moved between a first position (shown in FIGS. 4A, 4B, 5A, 6A-6D, and 7A) and a second position (shown in FIGS. 4C, 5B, 6E, and 7B). In the first position, the sleeves 280 may be biased toward a rolled configuration, such that a respective one of the first or second end of the main body 210 is exposed for connection to the corresponding end of the native blood vessel. In the second position, the sleeves 280 may be biased toward an extended configuration, such that a surface 281 of the sleeve 280 (shown in FIG. 6E) is disposed opposite the outer surface 213 of the main body 210 proximate the respective one of the first or second ends and engages the seam 290. In some cases, the vascular device may include a first sleeve proximate the first end of the main body 210 and a second sleeve proximate the second end, as depicted in FIGS. 4A-6E.

The sleeves 280 may be configured to promote hemostasis of the suture line or seam 190 for minimizing endoleaks proximate the respective end, for example, as a result of the sleeve resting against the seam once the vascular device is in place. For example, blood may have a tendency to leak through gaps between the end of the main body and the corresponding end of the aorta after the two are sutured together. Due to the presence of the sleeve 280 against the seam 290, however, any such blood seepage is slowed down, and eventually blood that has seeped through the seam 290 toward the sleeve 280 should clot and, in turn, serve to further protect against any additional leakage, in essence sealing the seam 290 against endoleaks. Thus, in some embodiments, the sleeves 280 may be configured to extend past the respective end of the main body 210, so as to provide coverage for the area of the seam 290.

Moreover, in some cases, the sleeve 280 may be biased inwardly (e.g., toward the seam 290) or may otherwise exert a clamping force (by itself or when used in conjunction with a separate tie or lasso disposed circumferentially on an exterior of the sleeve) once the sleeve is in the second position shown, for example in FIG. 6E. Accordingly, in the second position, the sleeve 280 may be configured to apply pressure in a direction toward the seam 290, so as to promote hemostasis for minimizing endoleaks, as well as to resist returning to the first position (FIGS. 6A-6D).

Similarly, with reference to FIG. 9, in embodiments in which a sleeve 300 is provided that is separate from the vascular device 200, the sleeve may initially be in a ring-like rolled up configuration and may be passed over the outer surface of the main body of a vascular device (such as the device 100 shown in FIGS. 2A-2C). Once in place near a respective end of the main body 110, the sleeve 300 of FIG. 9 may be unrolled to extend over and cover a suture line, such as the seam 290 shown in FIGS. 7A-7B. The sleeve 300 may be configured to include one or more ties 310, which may be wires or sutures embedded in or otherwise affixed to the sleeve 300, such as via panels 320 provided on the surface of the sleeve 300 through which the ties 310 are threaded. After the sleeve 300 is in place and unrolled over the relevant seam, the ties 310 may be cinched by a user to apply pressure to the area of the seam and promote clotting to minimize the likelihood or extent of endoleaks.

In either case, the sleeve 280, 300 may be made of Gore-Tex® fabric, polymer, or other material that can be configured to achieve the first and second positions described above and is also configured to hug the seam 290 in the second position so as to reduce the occurrence or extent of endoleaks at the seam.

Turning now to FIGS. 6A-6E, in some embodiments, at least one of the first 212 or second 214 ends of the main body 210 may comprise a flare. The flare may be a section of the main body 210 at the respective end 212, 214 that has a gradually increasing diameter in the direction of the respective end, as shown. For example, in the depicted embodiment in which the vascular device 200 has a tubular configuration, the respective flares may be trimmable by a user (e.g., the surgeon) so as to adjust, a diameter of the respective first or second end to correspond to and accommodate a diameter of the corresponding end of the native blood vessel to be joined to the respective end of the main body.

In some embodiments, each flared end of the main body 210 may extend away from a central axis A of the vascular device 200 (shown in FIG. 2A). As a result of the flare, the diameter of the main body 210 at a central location with respect to the two ends (e.g., between the sleeves 280 in FIG. 6A) may be less than the diameter of the main body at either end. For example, in some embodiments, the diameter of the main body 210 at the central location may be approximately between 20 mm and 40 mm, while the diameter of the flares at the ends 212, 214 of the main body may be approximately between 30 mm and 60 mm.

Providing flares at the first and second ends 212, 214 of the main body 210 in the manner described above may allow for a "one-size-fits-all" vascular device, or at least may minimize the number of different sizes of devices that need to be made available to accommodate patients with different anatomies. In this regard, the physician may be able to customize the vascular device 200 to fit a particular patient's anatomy by trimming one or both ends 212, 214 of the device to effectively reduce the diameter of the main body at the respective end of the device to match the diameter of the corresponding end of the native blood vessel to which it will be attached. For example, in a patient with a relatively large diameter aorta, a very small portion of the respective ends 212, 214 of the device 200 may be trimmed (or not at all) to allow the diameter of the main body 210 to correspond to the diameter of the native aorta, whereas in a patient with a relatively small diameter aorta, a larger portion of the respective ends of the device may be trimmed to allow the device to achieve a proper fit. Accordingly, in the example depicted in FIG. 6A, a section X of the first end 212 of the main body 210 has been trimmed by the surgeon to adjust a diameter of the first end and accommodate a diameter of the corresponding end of the native blood vessel to be joined to the first end. In this example, the trimmed section X will be discarded.

Thus, in the embodiment of FIGS. 6A-6E, the vascular device 200 is disposed in a patient's body (e.g., during open heart surgery) to replace a hemiarch portion of the patient's aorta. As described above, embodiments of the vascular device 200 (as depicted in FIG. 4A, for example) include a main body 210 having a first end 212 and a second end 214 and a secondary body 220 having a free end 222 and a fixed end 224, where the fixed end of the secondary body is engaged with an inner surface of the main body to limit movement of the fixed end in an axial direction.

In some cases, the surgeon may connect the first end 212 of the main body 210 with a corresponding end of a native blood vessel, as shown in FIG. 6B. Because the end 212 of the main body 210 in some embodiments is flared, in some cases the surgeon may trim a portion of the respective flare (section X in FIG. 6A) to adjust the diameter of the respective end to correspond to and accommodate the diameter of the corresponding end of the native blood vessel to be joined to the respective end of the main body, as shown in FIG. 6A.

Once the first end 212 of the main body 210 has been connected with a corresponding end of the native blood vessel, such as via suturing at the seam 290 as shown in FIG. 6B, the vascular device 200 may be moved from a retracted configuration, in which the secondary body 220 is at least partially contained within the main body 210 and the free end 222 is on a proximal side of the fixed end 224 (as shown in FIG. 6B) to an extended configuration, in which the secondary body 220 is extended distally from the main body 210 and the free end 222 is on a distal side of the fixed end 224 (as shown in FIG. 6D, with FIG. 6C illustrating an intermediate step in the process of everting the secondary body 220). The secondary body 220 may be pushed through the main body 210, from the position shown in FIG. 6B to the position shown in FIG. 6C to the position shown in FIG. 6D, by a surgeon using his finger or a surgical tool to apply a longitudinal force on the free end 222 of the secondary body 220 (e.g., in the direction B shown in FIG. 2A with respect to the free end 122).

After the secondary body 220 has been everted and the vascular device 200 is in the extended configuration, in some embodiments a sleeve 280 of the vascular device may be moved from a first position, in which the sleeve 280 is biased toward a rolled configuration such that a respective one of the first or second ends of the main body 210 is exposed for connection to the respective end of the native blood vessel (as shown in FIGS. 6A-6D), to a second position (shown in FIG. 6E). In the second position, the sleeve 280 is biased toward an extended configuration such that a surface of the sleeve is disposed opposite an outer surface of the main body 210 proximate the respective one of the first or second ends and engages the seam 290 defined between the respective end of the main body and the corresponding end of the native blood vessel, as described above. Thus, in the embodiment depicted in FIG. 6E, a first sleeve 280 disposed proximate the first end of the main body 210 is moved to engage the seam 290 defined between the first end of the main body and the corresponding end of the native blood vessel (e.g., while the other sleeve 280 proximate the second end of the main body is left in the first position for the time being).

Turning to FIG. 7A, in some embodiments, as described above, the secondary body 220 may be rotated by the surgeon about a longitudinal axis of the main body 210 to align an opening 250 defined through an outer surface of the secondary body with one or more aortic branches 14, 15, 16 of the patient's aortic arch. For example, in FIG. 7A, the secondary body 220 needs to be rotated in the direction of the arrow with respect to the main body 210 in order to achieve an appropriate alignment between the opening 250 and the opening of each of the three branches 14, 15, 16 shown. The rotation in this example would position the opening 250 at the base of the three branches 14, 15, 16, as shown in FIG. 7B, such that blood is able to flow from the heart, through the main body 210, into the secondary body 220, out the opening 250, and into each of the three branches 14, 15, 16 to perfuse distal regions of the patient's body.

Although rotation of the secondary body 220 shown in FIGS. 7A and 7B, and described above, is depicted as occurring while the vascular device 200 is in the extended configuration (e.g., after the secondary body has been everted), in some cases, the secondary body may be rotated while the vascular device is in the retracted configuration shown in FIG. 6B (e.g., before eversion), either instead of rotation after eversion or in addition to rotation after eversion. Moreover, in some cases, a lock 270 (shown in FIG. 7A) may be actuated from outside the vascular device to maintain the secondary body 220 in a rotationally fixed position with respect to the main body once the secondary body is rotated to a desired alignment with respect to the aortic branches of the patient's aortic arch, as described above. In such cases, rotation of the secondary body 220 may occur before the sleeve 280 is moved to the second position in which it overlies the seam 290, as the location of the lock 270 may be such that once the sleeve 280 is extended from the rolled configuration, as shown in FIG. 7B, the lock 270 is covered by the sleeve and is no longer accessible. In this regard, in some cases, the sleeve 280 may be configured to serve the additional purpose of keeping the lock 270 engaged with the secondary body 220, thereby maintaining the rotational position of the secondary body fixed with respect to the main body 210.

In some embodiments, the secondary body 220 may be configured such that it has a length that is longer than a length of the main body 210. In this way, in the retracted configuration shown in FIG. 6A, for example, the free end of the secondary body 220 (shown here in broken lines) may extend past a corresponding end (e.g., the second end 214) of the main body 210). Accordingly, the surgeon may in such cases have the flexibility of customizing the length of the secondary body 220 to achieve a length that is appropriate for addressing conditions in a corresponding portion of the aorta downstream of the location of the main body 210. In other words, the surgeon may, in some embodiments, be able to trim a portion of the free end of the secondary body 220 (e.g., while the vascular device is in the retracted configuration) so as to achieve a desired length of the secondary body that can be extended to engage a corresponding length of the aorta downstream and distal to the location of the main body 210, as indicated by the broken lines in FIG. 6E, for example. Moreover, with reference to FIG. 7B, once the secondary body 220 is in place and aligned with the aortic branches 14, 15, 16, the secondary body may be balloon expanded to further adjust a diameter of the secondary body to correspond to the diameter of the native blood vessel within which it is positioned so as to achieve a good fit within the walls of the vessel, thereby supporting the walls of the vessel and minimizing the risk of endoleaks (e.g., in the area of the branches).

Once the first end of the main body 210 has been connected to the corresponding end of the blood vessel and the secondary body 220 has been appropriately engaged with the blood vessel and any aortic branches, as described above, the second end 214 of the main body 210 may be connected to the corresponding end of the blood vessel, proximate the heart, as shown in FIGS. 8A-8C. Thus, as described above with respect to the first end of the main body 210, the second end 214 may also comprise a flare and may be trimmed to achieve an appropriate diameter suitable for joining to the diameter of the corresponding end of the blood vessel. The trimmed end 214 may then be sutured to the corresponding end of the blood vessel at the seam 290, as shown in FIG. 8A, and in some embodiments a sleeve 280 proximate the second end 214 may be moved from a first position, in which it is in a rolled configuration (FIG. 8B), to a second, extended configuration, in which it overlies the seam 290 (FIG. 8C). In this way, a pathway may be provided for blood flow from the patient's heart to vasculature distal to the heart via the main body 210 and the secondary body 220 of the vascular device.

Embodiments of the vascular device 100, 200 described above may be made of various materials and may be configured (e.g., have a length, diameter, cross-sectional shape, etc.) in different ways based on the particular condition of the patient, the application, the procedure to be used, the surgeon's preferences, etc. In some cases, for example, the main body 110, 210 may have an end-to-end length of between approximately 3 cm to approximately 15 cm, and this length may be trimmable by the surgeon at the time of the procedure via trimming of the ends, as described above. The secondary body 120, 220 may be configured to have a length (e.g., from the free end 122, 222 to the fixed end 124, 224) of approximately 5 cm to approximately 40 cm, and this length may also be trimmable by the surgeon as described above. Furthermore, in some cases, vascular devices may be available with a secondary body having a length in increments of 5 cm from approximately 5 cm to approximately 40 cm, such that the surgeon may choose an appropriate length based on the expected condition of the patient's vasculature (e.g., a vascular device with a secondary body that is about 30 cm long) and may be able to adjust the length by trimming the free end of the secondary body down to the appropriate length at the time of the procedure.

The main body 110, 210 of the vascular device 100, 200 may be configured to have a diameter of between approximately 30 mm to approximately 45 mm and, in some embodiments, may be available in sizes within this range in increments of 5 mm (e.g., 30 mm, 35 mm, 40 mm, 45 mm). The secondary body 120, 220 may be configured to have a diameter of approximately 25 mm to approximately 45 mm and, in some embodiments, may be available in sizes within this range in increments of 5 mm or 10 mm (e.g., 25 mm, 35 mm, 45 mm).

In some cases, the main body 110, 210 and the secondary body 120, 220 of the vascular device 100, 200 may be made of the same material, for example, a polymer material, such as polyester, Dacron® material, polytetrafluoroethylene (PTFE), and/or Gore-Tex® fabric. The polymer material may, in some cases, be structurally reinforced via a metal mesh, such as via stainless steel, Nitinol, or other biocompatible metal.

In other cases, the main body 110, 210 and the secondary body 120, 220 of the vascular device 100, 200 may be made of different materials, and sections of the main body or the secondary body may also be made of different materials (e.g., more than one material or structure may be used for the main body and/or the secondary body). For example, the main body 110, 210 may be a graft made of a polymer material, such as polyester, Dacron® material, polytetrafluoroethylene (PTFE), and/or Gore-Tex® fabric. The polymer material of the main body 110, 210 may, in some cases, be structurally reinforced via a metal mesh, such as via stainless steel, Nitinol, or other biocompatible metal. The secondary body 120, 220 may, in some cases, be a stent made of a metal mesh (e.g., stainless steel, Nitinol, or other biocompatible metal), or in other cases may be an endograft made of a metal mesh (e.g., stainless steel, Nitinol, or other biocompatible metal) that is surrounded by a polymer fabric, such as Gore-Tex® fabric. In still other embodiments, the secondary body 120, 220 may be configured to have a stent section (e.g., a section made of a metal mesh) in the region of the opening 150, 250 shown in the figures. In this way, the stent section may be configured to be balloon expandable, such that the region of the opening 150, 250 can be balloon expanded to engage the inner wall of the blood vessel in which the stent section is placed and achieve better engagement with the aortic branches surrounded by the opening. Moreover, the mesh may be configured to promote thrombosis, such that blood may clot in the areas surrounding the hole and promote a better seal between the opening 150, 250 and the native vessel in the area of the aortic branches. Other sections of the secondary body 120, 220, however, may be endograft sections made of metal mesh that is surrounded by a polymer fabric.

In still other embodiments, some or all of the main body 110, 210 and/or the secondary body 120, 220 may be made of a layered material. For example, the material may have an inner layer closest to the central axis of the vascular device (e.g., contacting the flow of blood), a middle layer, and an outer layer (e.g., serving as or contacting the wall of the native vessel). In such embodiments, the inner layer may be made of a relatively thin Gore-Tex® fabric or PTFE. The inner layer may be configured to be biocompatible and to promote generation of a new vascular wall (e.g., neoentima). The middle layer may be made of a metal mesh or other supportive structure and may be configured to provide structural support to the respective portion of the device. The outer layer may be made of a Gore-Tex® fabric (e.g., thicker than the inner layer) in some embodiments. In some cases, trimmable areas of the main body 110, 210 and/or the secondary body 120, 220 may include bare portions of mesh (e.g., ring patches of mesh between portions of the three layer material), such that the surgeon may trim the main body and/or the second body by cutting in the mesh portions.

One example of a method for treating a vascular abnormality in a patient's hemiarch using embodiments of the vascular device 100, 200 is provided above, although different variations of the described method may be used depending on the anatomy and condition of the patient, the particular vascular pathology being treated, and the surgeon's preferences.

Moreover, although the description herein uses the example of a device that is configured for treatment of a target site in the hemiarch (e.g., extending to the area of the innominate artery, the left common carotid artery, and the left subclavian artery), conditions in other areas of the aorta may also be addressed using embodiments of the vascular device, such as in other areas of the aorta where a portion of the aorta must be resected and replaced.

Embodiments of the vascular device described above may provide several advantages for the treatment of vascular abnormalities such as aneurysms and dissections, including abnormalities requiring resection of the hemiarch and treatment of the patient's vasculature downstream of the resected portion. For example, embodiments of the device may be provided that are configured to fit a greater patient population without the need for multiple sizes of devices, such as when flared ends are provided that can be customized at the time of the procedure to accommodate the particular patient's anatomy. Moreover, embodiments of the device may be used to replace a portion of the hemiarch and address conditions downstream of the hemiarch (e.g., in the aortic arch or descending aorta) with a single integrated device and without the need for multiple devices or multiple surgical procedures. In addition, bleeding at the interface between the device and the native vessels (e.g., where the device is sutured to the native vessels) may be significantly reduced, as described above, allowing for a more hemostatic procedure.

The devices and methods depicted in the figures and described above represent only certain configurations of the vascular device and method of using the device. The particular configurations and methods of delivery will depend on the patient's anatomy, the condition and location of the target site, the preferences of the practitioner, and other considerations. Moreover, features and aspects described above with respect to one of the depicted embodiments of the vascular devices 100, 200 may be used in combination with or instead of other features or aspects described above with respect to the other of the depicted embodiments of the vascular devices 100, 200. In general, it is to be understood that a vascular device described herein can have any combination of properties or features described herein not inconsistent with the objectives of the present disclosure. Similarly, a method described herein can also include any combination of steps and/or use any vascular device described herein not inconsistent with the objectives of the present disclosure.

Many modifications and other embodiments of the invention will come to mind to one skilled in the art to which this disclosure pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A vascular device configured for replacing at least part of a patient's hemiarch, the vascular device comprising:
   a main body having a first end and a second end, wherein each of the first and second ends is configured to be attached to a corresponding end of a native blood vessel to provide a pathway for blood flow from the patient's heart to vasculature distal to the heart;
   a secondary body having a free end and a fixed end, wherein the fixed end is attached to an inner surface of the main body to limit movement of the fixed end in an axial direction; and
   wherein the vascular device is configured to be moved from a retracted configuration, in which the secondary body is at least partially contained within the main body and the free end is on a proximal side of the fixed end, to an extended configuration, in which the secondary body is extended distally from the main body and the free end is on a distal side of the fixed end, and
   wherein, in the extended configuration, the secondary body is configured to engage downstream portions of the patient's aorta with respect to a position of the main body.

2. The vascular device of claim 1, wherein the secondary body defines an opening through an outer surface thereof configured to surround one or more aortic branches of the patient's aortic arch.

3. The vascular device of claim 1, wherein the fixed end of the secondary body is attached to the inner surface of the main body so as to allow the secondary body to rotate about a longitudinal axis of the main body.

4. The vascular device of claim 3, wherein the inner surface of the main body comprises a track, and wherein the fixed end of the secondary body comprises a guide configured to ride within the track such that the secondary body is rotatable with respect to the main body.

5. The vascular device of claim 3 further comprising a lock, wherein the lock is configured to be actuatable by a user from outside the vascular device and wherein the lock is configured to maintain the secondary body in a rotationally fixed position with respect to the main body.

6. The vascular device of claim 1, wherein at least one of the first end and the second end of the main body comprises a flare, such that the respective flare is trimmable by a user to adjust a diameter of the respective first end or second end to correspond to and accommodate a diameter of the corresponding end of the native blood vessel to be joined to the respective end of the main body.

7. The vascular device of claim 1 further comprising at least one sleeve configured to extend over a seam defined between a respective end of the main body and the corresponding end of the native blood vessel.

8. The vascular device of claim 7, wherein the at least one sleeve is attached to an outer surface of the main body.

9. The vascular device of claim 7, wherein the at least one sleeve is configured to be moved between a first position and a second position, wherein in the first position the at least one sleeve is biased toward a rolled configuration, such that a respective one of the first or second end of the main body is exposed for connection to the corresponding end of the native blood vessel, and in the second position the sleeve is biased toward an extended configuration, such that a surface of the sleeve is disposed opposite an outer surface of the main body proximate the respective one of the first or second ends and engages the seam.

10. The vascular device of claim 7, wherein the vascular device comprises a first sleeve proximate the first end and a second sleeve proximate the second end.

11. The vascular device of claim 1, wherein the secondary body has a length that is longer than a length of the main body, such that, in the retracted configuration, the free end of the secondary body extends past a corresponding end of the main body.

12. A method for replacing at least part of a patient's hemiarch using a vascular device, the method comprising:
    disposing a vascular device in a patient's body for replacing a hemiarch portion of the patient's aorta, wherein the vascular device comprises a main body having a first end and a second end and a secondary body having a free end and a fixed end, wherein the fixed end of the secondary body is attached to an inner surface of the main body to limit movement of the fixed end in an axial direction;
    connecting the first end of the main body to a corresponding end of a native blood vessel;
    moving the vascular device from a retracted configuration, in which the secondary body is at least partially contained within the main body and the free end is on a proximal side of the fixed end, to an extended configuration, in which the secondary body is extended distally from the main body and the free end is on a distal side of the fixed end; and
    connecting the second end of the main body to a corresponding end of the native blood vessel.

13. The method of claim 12 further comprising rotating the secondary body about a longitudinal axis of the main body to align an opening defined through an outer surface of the secondary body with one or more aortic branches of the patient's aortic arch.

14. The method of claim 13, wherein the secondary body is rotated while the vascular device is in the retracted configuration.

15. The method of claim 13 further comprising actuating a lock from outside the vascular device to maintain the secondary body in a rotationally fixed position with respect to the main body once the secondary body is rotated to a desired alignment with respect to the aortic branches of the patient's aortic arch.

16. The method of claim 12, wherein at least one of the first end and the second end of the main body comprises a flare, the method further comprising trimming a portion of the respective flare to adjust a diameter of the respective first or second end to correspond to and accommodate a diameter of the corresponding end of the native blood vessel to be joined to the respective end of the main body.

17. The method of claim 12 further comprising trimming a portion of the free end of the secondary body.

18. The method of claim 12 further comprising moving a sleeve of the vascular device from a first position, in which the sleeve is biased toward a rolled configuration such that a respective one of the first or second ends of the main body is exposed for connection to the respective end of the native blood vessel, to a second position, in which the sleeve is biased toward an extended configuration such that a surface of the sleeve is disposed opposite an outer surface of the main body proximate the respective one of the first or second ends and engages a seam defined between a respective end of the main body and the corresponding end of the native blood vessel.

19. The method of claim 18, wherein moving a sleeve of the vascular device comprises moving a first sleeve disposed proximate the first end of the main body to engage a seam defined between the first end of the main body and the corresponding end of the native blood vessel.

20. The method of claim 19 further comprising connecting the second end of the main body with a corresponding end of the native blood vessel, such that a pathway is provided for blood flow from the patient's heart to vasculature distal to the heart via the main body and the secondary body.

* * * * *